(12) United States Patent
Defez

(10) Patent No.: US 9,157,104 B2
(45) Date of Patent: Oct. 13, 2015

(54) METHOD TO IMPROVE PHOSPHATE SOLUBILIZATION IN PLANTS

(75) Inventor: Roberto Defez, Napoli (IT)

(73) Assignee: Consiglio Nazionale delle Ricerche, Rome (RM) (IT)

( * ) Notice: Subject to any disclaimer, the term of this patent is extended or adjusted under 35 U.S.C. 154(b) by 965 days.

(21) Appl. No.: 13/257,852

(22) PCT Filed: Mar. 23, 2010

(86) PCT No.: PCT/IB2010/051249
§ 371 (c)(1),
(2), (4) Date: Oct. 20, 2011

(87) PCT Pub. No.: WO2010/109408
PCT Pub. Date: Sep. 30, 2010

(65) Prior Publication Data
US 2012/0040828 A1   Feb. 16, 2012

(30) Foreign Application Priority Data
Mar. 23, 2009  (IT) ................... RM09A0128

(51) Int. Cl.
| | | |
|---|---|---|
| C12P 3/00 | (2006.01) | |
| C12N 1/20 | (2006.01) | |
| C12N 15/00 | (2006.01) | |
| C07H 21/04 | (2006.01) | |
| C12P 17/10 | (2006.01) | |
| C05F 11/08 | (2006.01) | |

(52) U.S. Cl.
CPC ............... *C12P 17/10* (2013.01); *C05F 11/08* (2013.01); *C12P 3/00* (2013.01)

(58) Field of Classification Search
CPC .......... C12P 3/00; C12N 9/80; C12N 9/0069; C12N 15/73
See application file for complete search history.

(56) References Cited

U.S. PATENT DOCUMENTS
7,846,708 B2 * 12/2010 Defez ............................ 435/243

FOREIGN PATENT DOCUMENTS
WO   WO 2006/134623   * 12/2006

OTHER PUBLICATIONS

Abd-Alla et al. Solubilization of Rock Phosphates by Rhizobium and Bradyrhizobium. Folia Microbiol. 39(1), 53-56 (1994).*
Dias, et al., "Isolation of 1-12 micropropagated strawberry endophytic bacteria and assessment of their potential for plant growth promotion", World Journal of Microbiology and Biotechnology, Kluwer Academic Publishers, DO, vol. 25, No. 2, Oct. 19, 2008, pp. 189-195.
Pandey, et al., "Two-species microbial consortium for growth promotion of *Cajanus cajan*", Current Science (Bangalore), vol. 92, No. 8, Apr. 2007, pp. 1137-1142.
Rodriguez, et al., "Phosphate solubilizing bacteria and their role in plant growth promotion", Biotechnology Advances, Elsevier Inc. US, vol. 17, No. 4-5, Oct. 1999, pp. 319-339.
Camerini, et al., "Introduction of a novel pathway for IAA biosynthesis to rhizobia alters vetch root nodule development", Archives of Microbiology, Springer, Berlin, DE, vol. 190, No. 1, Apr. 16, 2008, pp. 67-77.
M. Datta, S. Banik and R. K. Gupta: "Studies on the efficacy of a phytohormone producing phosphate solubilizing *Bacillus firmus* in augmenting paddy yield in acid soils of Nagaland", Plant and Soil, 69, 365-373 (1982), Junk Publishers, the Hague, the Netherlands.

* cited by examiner

*Primary Examiner* — Yong Pak
(74) *Attorney, Agent, or Firm* — Lucas & Mercanti, LLP

(57) ABSTRACT

The present invention relates to the use of a bacterium having an high indole-3-acetic acid (IAA) content for solubilizing phosphate rock (PR) in the ground, wherein said bacterium is obtained by transformation with a gene encoding an agent able to increase the IAA content.

3 Claims, 7 Drawing Sheets

Figure 1:
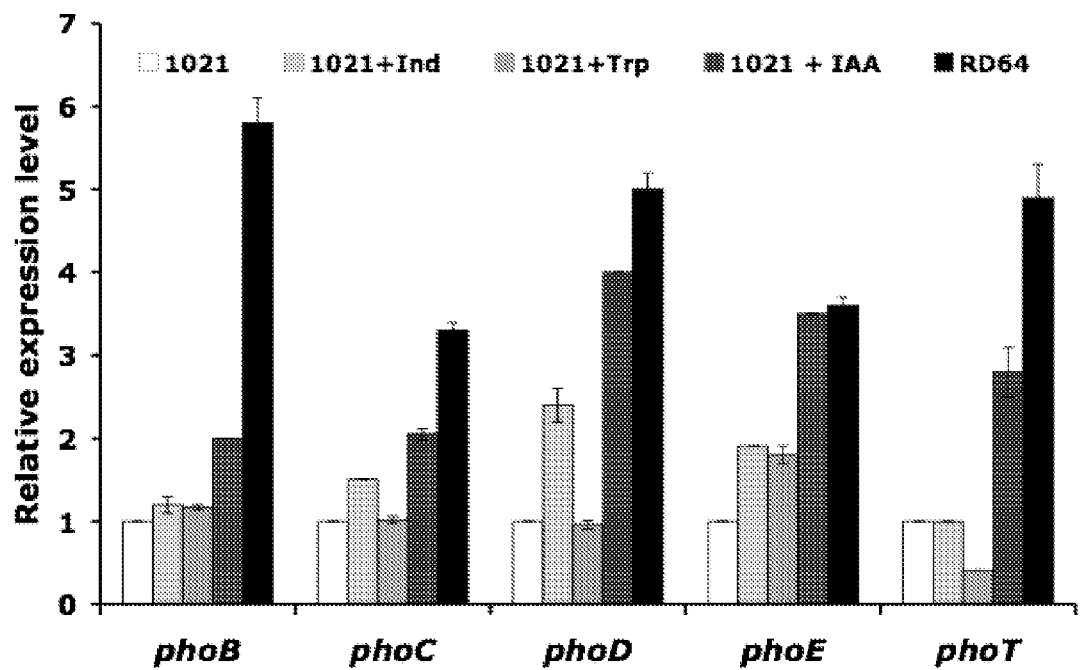

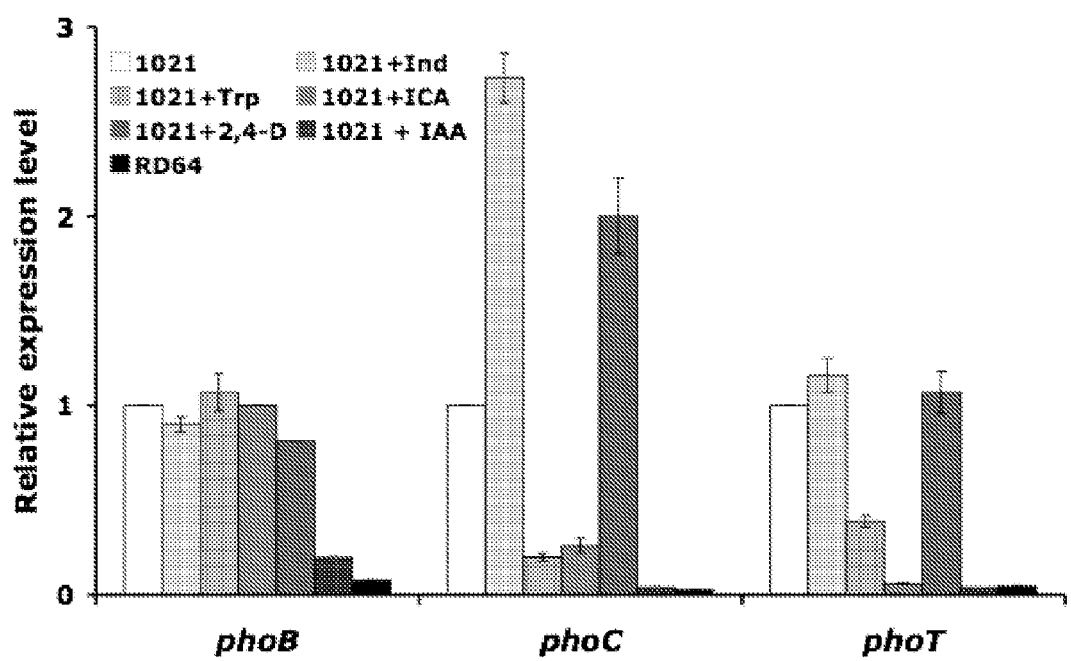
Fig. S1

A
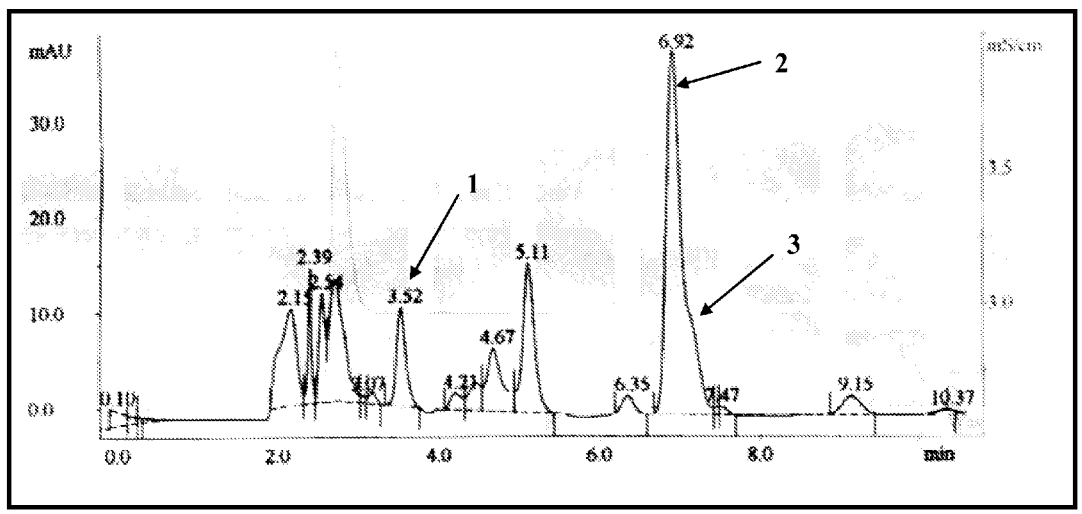
B
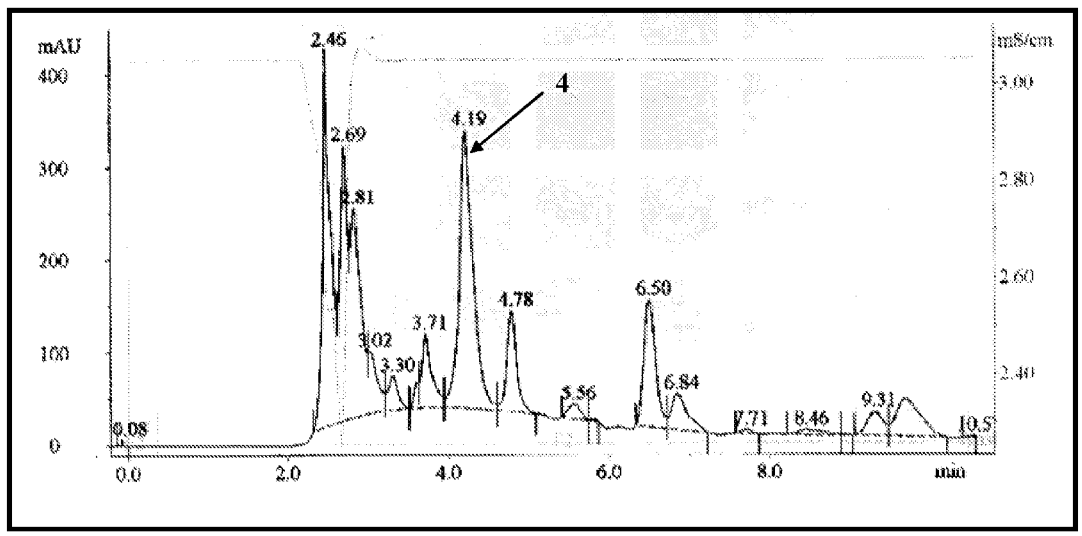
Fig. S2

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence

```
<220> FEATURE:
<223> OTHER INFORMATION: synthetic primer

<400> SEQUENCE: 1
ttacgtcgtc aagcccttct                                                    20

<210> SEQ ID NO 2
<211> LENGTH: 20
<212> TYPE: DNA
<213> ORGANISM: Artificial Sequence
<220> FEATURE:
<223> OTHER INFORMATION: synthetic primer

<400> SEQUENCE: 2
ccggtgagga catgagaaat                                                    20

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
actcctgcgc atgataaacc                                                    20

<210> SEQ ID NO 4
<211> LENGTH: 20
<212> TYPE: DNA
<213> ORGANISM: Artificial Sequence
<220> FEATURE:
<223> OTHER INFORMATION: synthetic primer

<400> SEQUENCE: 4
tgttgaggac gctcagtacg                                                    20

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
tatctcgttc ccctcgtcac                                                    20

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
acctttgtcg accatcttgc                                                    20

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
gcttcatcct gtgcttcctc                                                    20
```

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
agaccttcct ccggtttcat                                                    20

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
tggcgtcgtt ctttacatga                                                    20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
gtctcctttt cgagcgtgac                                                    20

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
cgagaggtga tgacggaagt                                                    20

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
accgactttc tcgcacagat                                                    20

<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
cttcagcatg aacgaccaga                                                    20

<210> SEQ ID NO 14
<211> LENGTH: 20
<212> TYPE: DNA
<213> ORGANISM: Artificial Sequence
<220> FEATURE:
<223> OTHER INFORMATION: synthetic primer

```
<400> SEQUENCE: 14
aagaaccgcg taaccttcct                                        20
```

METHOD TO IMPROVE PHOSPHATE SOLUBILIZATION IN PLANTS

CROSS-REFERENCE TO RELATED APPLICATIONS

This application is a 371 of PCT/IB2010/051249 filed Mar. 23, 2010, which claims the benefit of Italian Patent Application No. RM2009A000128 filed Mar. 23, 2009, the contents of each of which are incorporated herein by reference.

FIELD OF THE INVENTION

The present invention relates to the use of a bacterium with elevated levels of indole-3-acetic acid (IAA) for agricultural applications, for instance to improve agriculture yield and to increase the availability of fertilizers for vegetal growth.

BACKGROUND OF THE INVENTION

Nitrogen (N) and phosphorus (P) are the most limiting factors for plant growth. Some microorganisms improve the uptake and availability of N and P minimizing chemical fertilizers dependence.

Compared with the other major nutrients, such as nitrogen, phosphorus (P) is by far the least mobile and available to plants in most soil conditions. Although P is abundant in soils in both organic and inorganic forms, it is frequently a major or even the prime limiting factor for plant growth. Many soils throughout the world are P-deficient, because the free concentration (the form available to the plant), even in fertile soils, is generally low due to high reactivity of soluble P with calcium, iron, or aluminium that leads to P precipitation (36, 41). In addition, in developing countries chemical fertilizers, which provide the three major plant nutrients (N, P and potassium) are not widely used due to cost limitations. In these areas the direct application of ground Phosphate Rock (PR) is increasingly used, even if the P released from PR is often too low for crop growth (9, 38). It is known that many microorganisms, in particular of the genera *Pseudomonas, Bacillus* and *Rhizobium*, have the ability to change their metabolism in response to the phosphorus available for cellular growth. The switch in metabolism is mediated through the repression and induction of various genes whose products are involved in processes ranging from the uptake and acquisition of P sources to de novo synthesis of new cellular components (36, 18). Furthermore, in vitro studies showed that for some of these bacteria both the P-solubilizing activity and the production of the auxin indole-3-acetic acid (IAA) (39, 17) were observed, despite a direct correlation linking IAA production to P-solubilization was not demonstrated.

P uptake has been investigated in various microorganisms. Many bacteria, including *S. meliloti*, have at least two P transport systems, consistent with the high- and low-affinity transport systems. The high-affinity system is encoded by the phoCDET operon, and the low-affinity system is encoded by pit (in the orfA-pit operon). In *S. meliloti* the expression of genes encoding for both P transport systems is controlled by the PhoB activator. Under P-excess conditions, PhoB is inactive, and the phoCDET are not expressed. Under P-limiting conditions, the low-affinity Pit permease system is repressed by activated PhoB, while the high-affinity PhoCDET system is induced and becomes the primary mechanism of P transport (10). Many bacterial strains contain products pstSCAB homologs that function as high-affinity phosphate transporters. For *S. meliloti* 1021 a 1-bp deletion in the pstC ORF is probably responsible (via PhoB) for the moderate constitutive activation of 12 phosphate-starvation inducible genes, observed in the absence of phosphate stress (24, 43). In both plants and microorganisms, the primary mechanisms of PR solubilization are $H^+$ excretion, organic acids production and acid phosphatase biosynthesis (2, 3). Organic acids, including acetate, lactate, malate, oxalate, succinate, citrate, gluconate, ketogluconate, etc. can form complexes with the iron or aluminum in ferric and aluminum phosphates, thus releasing plant-available phosphate into the soil (18, 22). Organic acids may also increase P availability by blocking P absorption sites on soil particles or by forming complexes with cations on soil mineral surface (36).

Mineralization of most organic phosphorus compounds is carried out by means of phosphatase enzymes. The major source of these enzymes in soil is considered to be of microbial origin. In particular, phosphatase activity is substantially increased in the rhizosphere. The pH of most soils ranges from acids to neutral values. Thus, acid phosphatases should play the major role in this process (36).

In the present invention, the P-solubilizing ability of a *S. meliloti* 1021 strain, RD64, and its effect on the growth of *Medicago* host plant were analysed.

The author used the *S. meliloti-M. truncatula* system since the microarrays were available for the bacterium and *Medicago* is a well recognized model system for indeterminate nodule development.

The RD64 strain has been previously engineered to overproduce IAA (11, 35), showing that it is able to release into liquid growth media up to 78-fold more IAA compared to wild type 1021 (12, 21). It was also previously reported that, as found for IAA-treated *E. coli* cells (7), RD64 is more resistant to salinity and other abiotic stresses (5). *Medicago* plants nodulated by this strain have a higher degree of protection against oxidative damage induced by salt stress (5). Furthermore, it was previously shown that IAA triggers induction of tricarboxylic acid cycle or citric acid cycle, TCA cycle enzymes in quite distant systems such as transformed human cells (15), *E. coli* (8) and *S. meliloti* (21) with a mechanism not yet understood.

To evaluate the global effects triggered by IAA overproduction in *S. meliloti* RD64, the gene expression pattern of wild type 1021 was compared with that of RD64 and 1021 treated with IAA and other four chemically or functionally related molecules by microarray analysis.

Among the genes differentially expressed in RD64 and IAA-treated 1021 cells, the author found two genes of pho operon. This unexpected finding led them to examine the mechanisms for mineral P solubilization in RD64 and the potential ability of this strain to improve *Medicago* growth under P-starved conditions. P-starved conditions are defined when bacteria, either 1021 or RD64, grow in media containing 1.0 mM K-phosphate. An increase in acid phosphatase activity and organic acids excretion was observed for RD64 strain in free-living conditions. Furthermore, the amount of organic acids exuded from the roots of *Medicago* plants nodulated by this strain was higher than that measured for plants nodulated by the 1021 wild type strain. This effect was connected to the enhanced P solubilization and plant dry weight production observed for these plants.

DESCRIPTION OF THE INVENTION

In the present invention, a strain of *S. meliloti* 1021 was engineered to over-produce the phyto-hormone IAA using a plasmid pG-Promintron-iaaM-tms2, described in WO00/28051 (strain RD64). The skilled person in the art will understand that other strains may be engineered.

It was surprisingly found, in the present invention, that RD64 is highly effective in mobilizing P from insoluble sources such as phosphate rock (PR). Under P-limiting conditions, the higher P-mobilizing activity of RD64, as compared to 1021 wild type strain, is connected with the up-regulation of genes coding for the high-affinity P transport system, the induction of acid phosphatase activity and the increased secretion into the growth media of malic, succinic and fumaric acids. P-limiting conditions relate to a concentration of 5% PR when only bacteria were grow in a defined minimal media, or 0.02% PR when *Medicago* plants nodulated by either 1021 or RD64 were grown in defined minimal media. *Medicago truncatula* plants nodulated by RD64 (Mt-RD64), when grown under P limiting conditions, released higher amounts of another P-solubilizing organic acid, the 2-hydroxyglutaric acid, as compared to the plants nodulated by the wild-type strain (Mt-1021).

It has already been shown that Mt-RD64 plants exhibited a higher dry weight production as compared to Mt-1021 plants. Here the author reports that also P-limiting Mt-RD64 plants show a significant increase both in shoot and root fresh weight when compared to P-limiting Mt-1021 plants.

The author discusses how, in a *rhizobium*-legume model system, a balanced interplay of different factors linked to the bacterial IAA over-production rather than IAA production per se stimulates plant growth under stressful environmental conditions, and in particular, under P-limitation.

Thus, a soil bacterium such as RD64, able to provide solubilised P for plant growth is particularly advantageous to improve agricultural yield, in particular in tropical areas such as sub-Saharan areas where the use of chemical fertilizers is limited and where large sources of PR are available.

It is therefore an object of the present invention the use of a bacterium having an high indole-3-acetic acid (IAA) content for solubilizing phosphate rock (PR) in the ground, wherein said bacterium is obtained by transformation with a gene encoding an agent able to increase the IAA content.

Preferably said agent able to increase the IAA content is either an indolacetamide hydrolase (iaaM) or tryptophane monoxygenase (tms2) enzyme.

In a preferred embodiment the bacterium belongs to the genus *Rhizobium*.

Preferably said bacterium of the genus *Rhizobium* is of species *S. meliloti*.

Still preferably said bacterium is able to produce the indole-3-acetic acid (IAA) phytohormone.

Yet preferably, said bacterium is contained within leguminous plant nodules.

It is a further object of the invention a method to provide solubilized phosphorus to a plant able to nodulate and/or to the soil surrounding the growth of said plant comprising inducing the nodulation of said plant with a bacterium having an high indole-3-acetic acid (IAA) content, wherein said bacterium is obtained by transformation with a gene encoding an agent able to increase the IAA content.

Preferably said agent able to increase the IAA content is either an indolacetamide hydrolase (iaaM) or tryptophane monoxygenase (tms2) enzyme.

Preferably said bacterium belongs to the genus *Rhizobium*.

Yet preferably, said bacterium of the genus *Rhizobium* is of species *S. meliloti*.

Still preferably said bacterium is able to produce the indole-3-acetic acid (IAA) phytohormone.

Preferably said bacterium is contained within leguminous plant nodules.

The invention will be now illustrated by means of non limiting examples referring to the following figures.

FIG. S1. Quantitative RT-PCR analysis of pho operon genes in *S. meliloti* cells under P-sufficient conditions (13 mM K-phosphate). The relative expression level was >1 for genes more highly expressed in RD64 and in 1021 cells treated for 3 hours with 0.5 mM IAA, Ind, Trp, ICA and 2,4-D. The relative expression level was <1 for genes more highly expressed in 1021 cells (control). Error bars represent the standard deviation from three independent biological experiments.

FIG. 1. Quantitative RT-PCR analysis of pho operon genes expression in *S. meliloti* cells under P-starving conditions. The relative expression level was >1 for genes more highly expressed in RD64 and in 1021 cells treated for 3 hours with 0.5 mM IAA, Ind, Trp, ICA and 2,4-D. The relative expression level was <1 for genes more highly expressed in 1021 cells (control). Error bars represent the standard deviation from five independent biological experiments ($p<0.05$).

Figure 2:
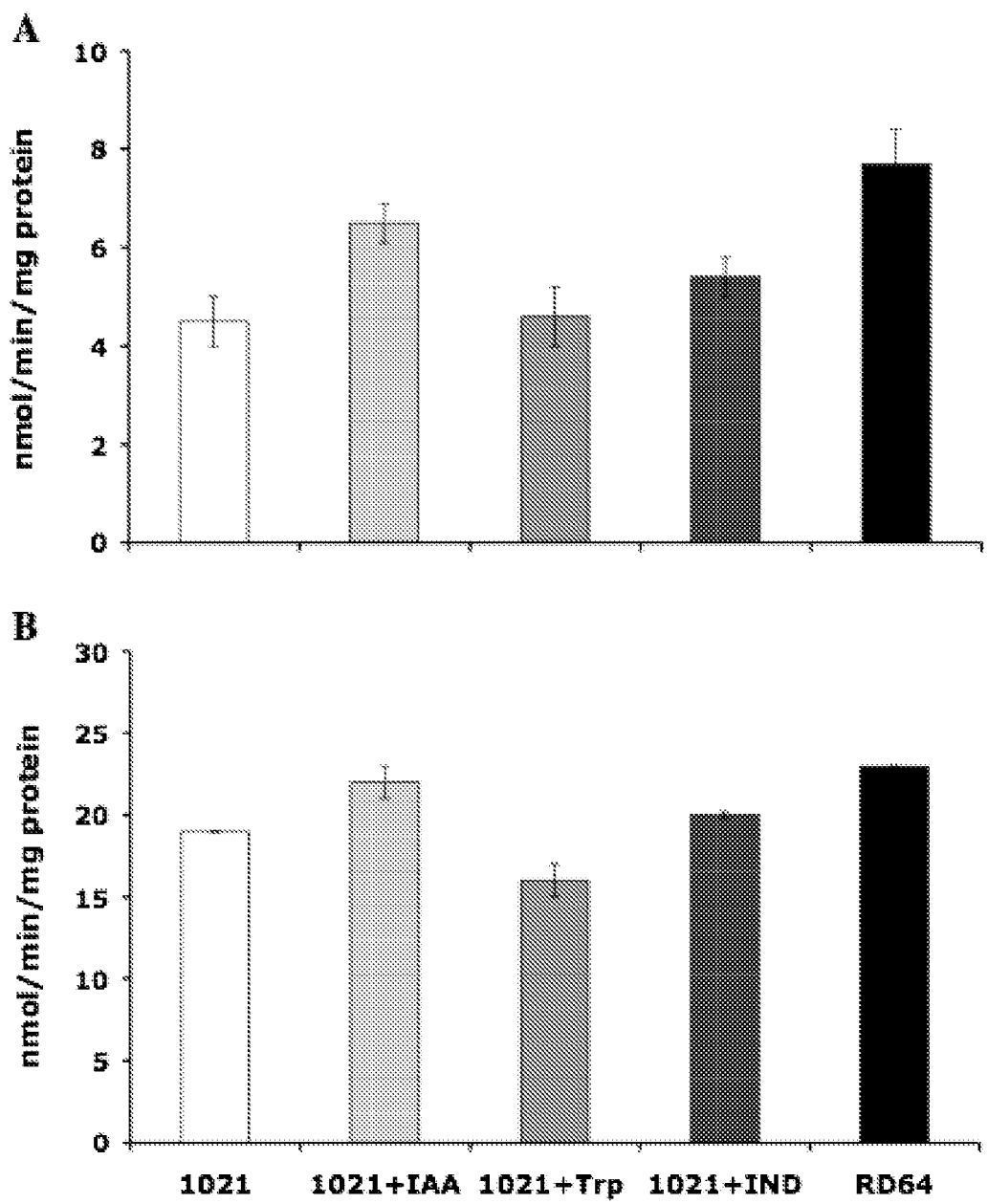

FIG. 2. Acid (A) and alkaline (B) phosphatase activity in *S. meliloti* cells under P-starved conditions. Log-phase cells grown in a MOPS-buffered minimal medium (starting P concentration=13 mM) were washed and then resuspended in the same medium containing no added P (1021 and RD64 strains) and 0.5 mM IAA, Trp or Ind (1021 strain). Treatments were performed for 3 hours at 30° C. Values are the means±SD of four independent biological experiments ($p<0.05$).

Figure 3:
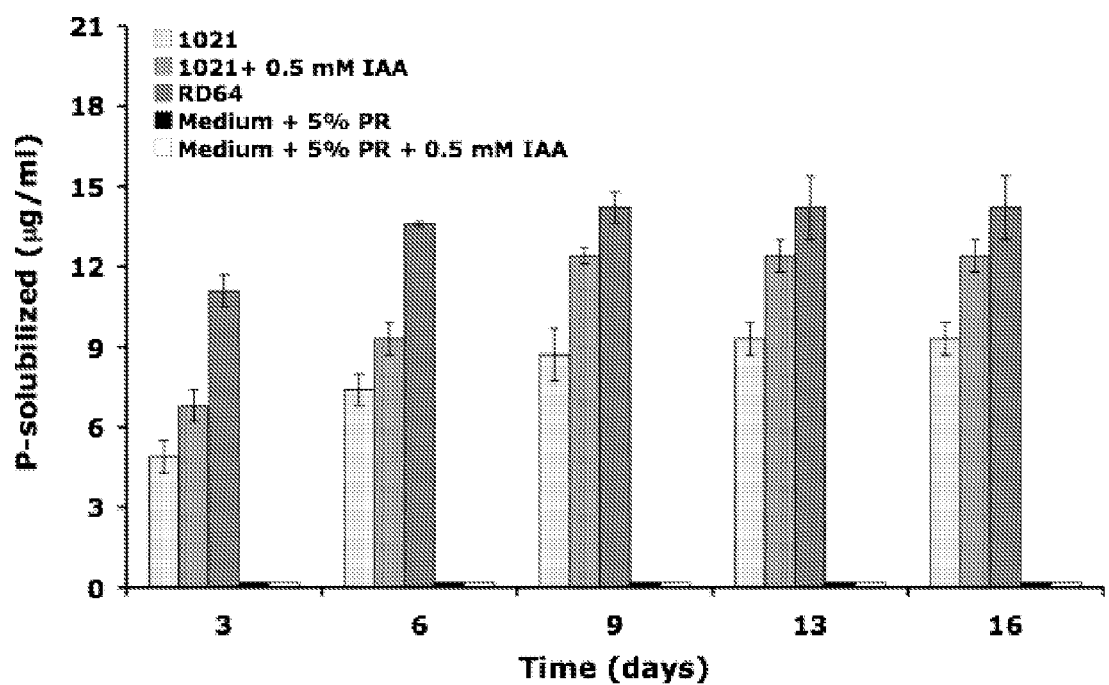

FIG. 3. Soluble phosphate release into *S. meliloti* cultures containing 5% PR as P source. Data are the mean±SD of four independent biological experiments ($p<0.006$).

FIG. S2. HPLC chromatograms at 210 nm of organic acids in (A) bacterial supernatants and (B) root exudates samples. The arrows point to peaks identified by GC-MS. The numbers correspond to the following acids: (1) malic, (2) succinic, (3) fumaric and (4) 2-hydroxyglutaric.

Figure 4:
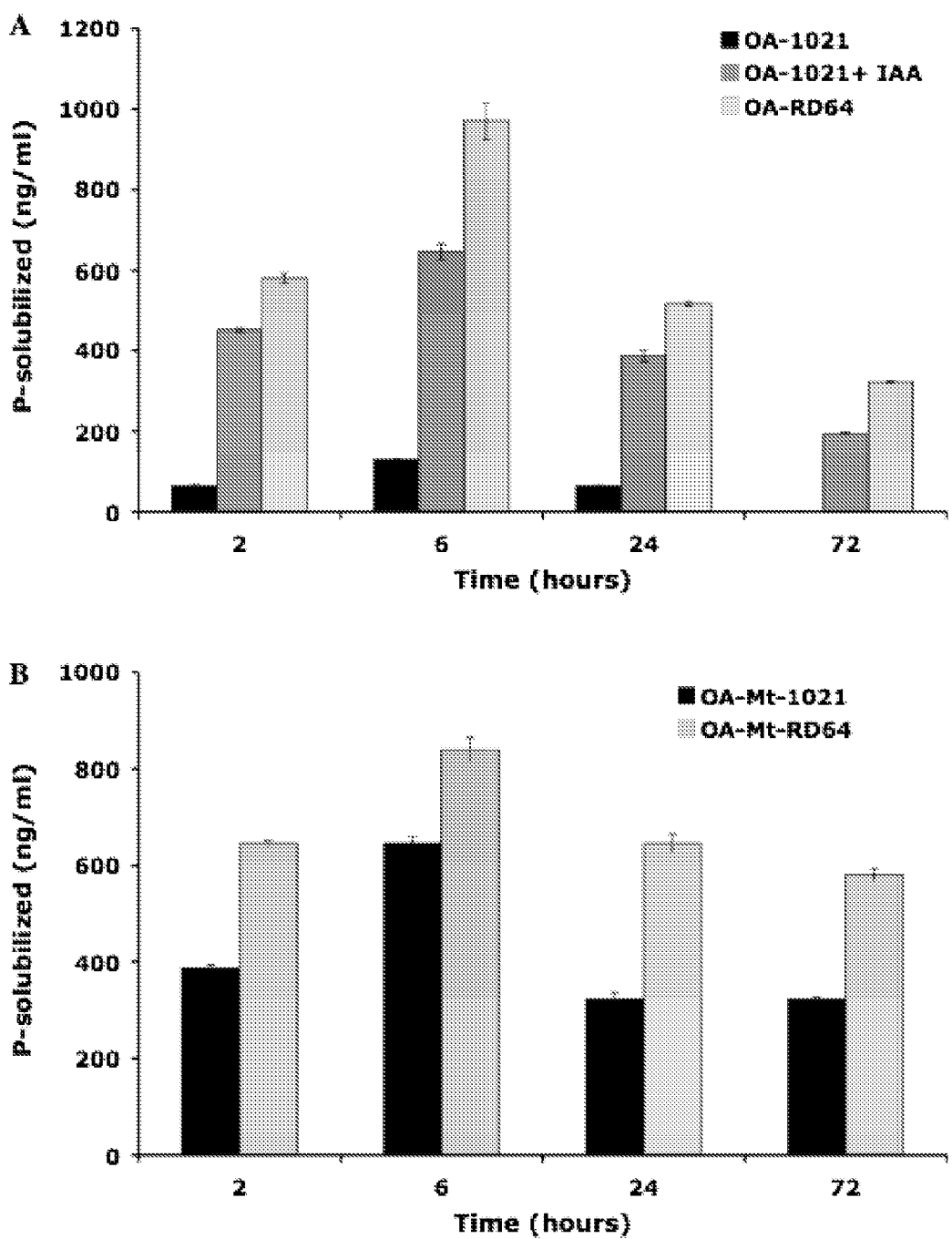

FIG. 4. Changes in soluble phosphate release into the bacterial free medium containing 5% phosphate rock (PR) as P source (P-limiting conditions for bacteria growing in a minimal media with PR). The organic acids (A) fumaric, malic and succinic were added to levels that simulate the amount released by 1021 (OA-1021), 1021 treated with 0.5 mM IAA (OA-1021+IAA) and RD64 cells (OA-RD64) into the growth media. The 2-hydroxyglutaric acid (B) was added to level that simulate the amount released by Mt-1021 (OA-Mt-1021) and Mt-RD64 (OA-Mt-RD64) plants into the growth media. The amounts of each added organic acids derived from the data obtained in HPLC analysis and were reported in the Material and Methods section. Data are the mean±SD of five independent biological experiments ($p<0.006$).

Figure 5:
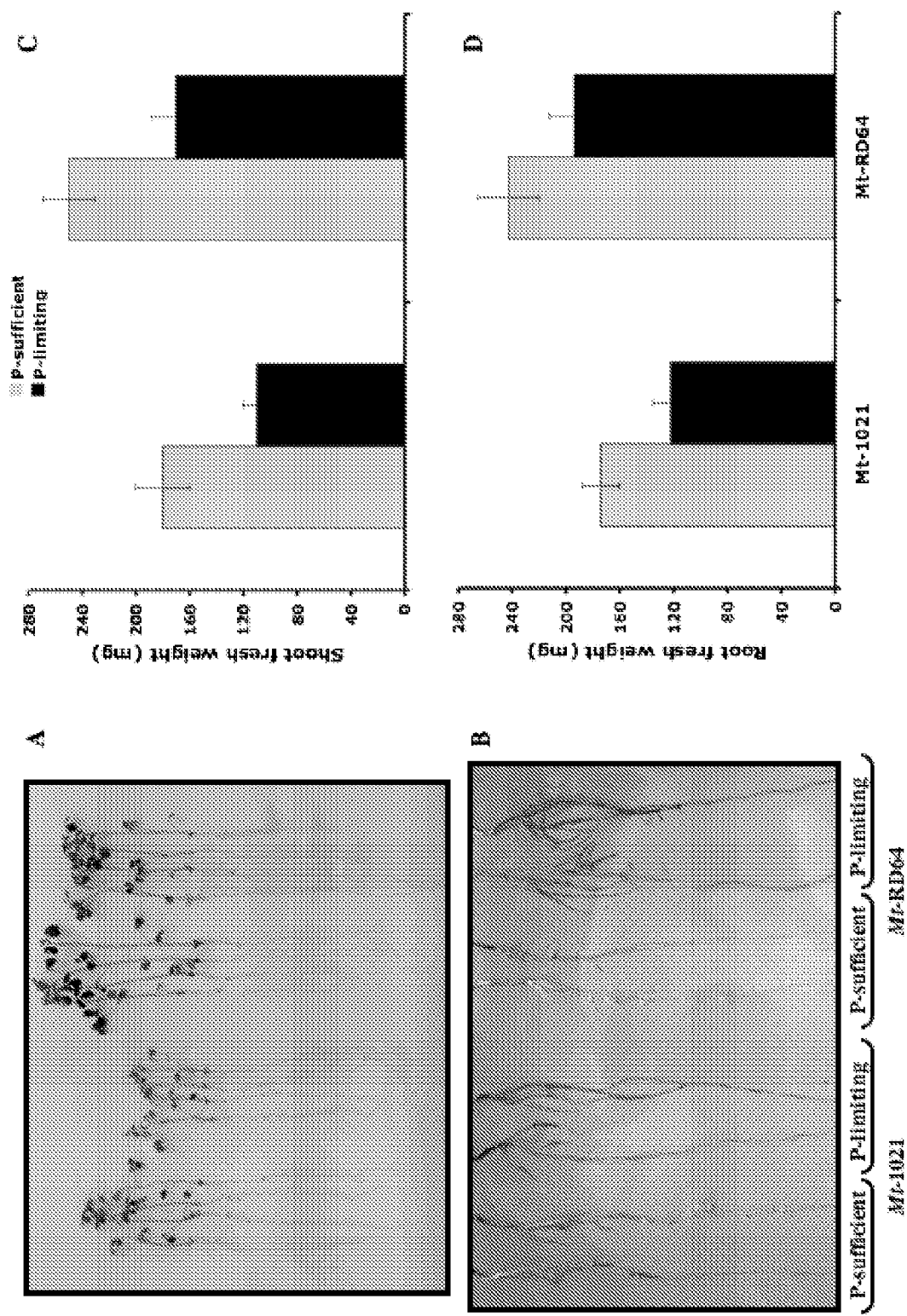

FIG. 5. Effect of bacterial IAA over-expression on *Medicago truncatula* growth. (A) Phenotype of plants grown for 4 weeks under P-limiting (0.02% PR) and P-sufficient conditions (more than 8 mM K-phosphate). (B) Roots phenotype of plants grown for 1 week as described in (A). (C) Shoot fresh weight, (D) root fresh weight of plants grown as described in (A). Data are the mean±SD ($n=30$, $p<0.001$).

MATERIALS AND METHODS

Bacterial Growth Conditions

The *S. meliloti* wild type 1021 strain and the IAA-overproducing RD64 strain containing the p-iaaMtms2 construct were previously described (12, 21). Standard mannitol minimal medium for *rhizobium* (RMM) (19) was modified to contain 1% (w/v) mannitol as carbon source, 1% (w/v) ammonium chloride, 10 mM morpholine propanesulfonic acid (MOPS; pH 7.0) to buffer and P ($KH_2PO_4$) added to a final concentration of 1 mM (P-starvation) and 13 mM (P-sufficient). Antibiotics were included as required (5).

P-Depletion

For P starvation experiments, cells of 1021 wild-type and RD64 strains were grown at 30° C. to mid exponential phase ($OD_{600}$=0.6) in RMM broth containing 1% (w/v) mannitol as carbon source and 13 mM P, washed with RMM containing 0 P, resuspended in the same medium and then divided into three cultures. No P (−P), 1.0 mM P (P-starved cells) or 13 mM P (+P cells also named P-sufficient cells) was added into the three cultures, respectively. The P-starved and P-sufficient 1021 wild type cells were treated for 3.0 hours with 0.5 mM IAA. To test the specificity of IAA-effects, other four selected compounds [indole (Ind), tryptophan (Trp), indole-3-carboxylic acid (ICA) and 2,4-dichlorophenoxyacetic acid (2,4-D)], whose acidity covers a range that goes from the acid (pH 2.9) to the weak acid (pH 6.1), were dissolved in 50% (w/v) ethanol and added to P-starved and P-sufficient 1021 wild type cells to a final concentration of 0.5 mM. The newly introduced IAA biosynthetic pathway use Trp to produce IAA, thus opening the question of whether the RD64 cells are Trp starved. Indeed, as the authors introduced in the bacteria two new genes that convert Trp into IAA, the two genes might be very efficient so that as soon as a molecule of Trp is around they convert it into IAA and there is no Trp to be included into the protein synthesis. To rule out that this bacteria could be partially starved for Trp, RD64 cells were also treated with 0.5 mM Trp and used for microarrays and RT-PCR analyses. Finally, to avoid solvent interference, control cells were treated with similar amount of ethanol solution. After 3 hours of each treatment, cell batches were collected, freezed and stored at −80° C. for use in experiments.

For phosphate solubilization experiments 5% Moroccan phosphate rock (PR) (Sigma-Aldrich, cat. No. 32) was used as P source. When 5% PR is used as P source to allow bacterial growth this is described as a P-limiting condition. At least five independent experiments were always performed.

Microarray Analysis

Previously described methods were used to compare the gene expression patterns of 1021 untreated cells (control) with those of RD64, 1021+IAA, 1021+Ind, 1021+Trp, 1021+ICA and 1021+2,4-D cells grown under P-sufficient (13 mM) conditions as reported in Imperlini et al. (21).

RT-PCR Analysis

Total RNA from P-sufficient and P-starved cells was isolated as previously described (5). cDNA were synthesized with the StrataScript™ reverse transcription reagents (Stratagene) and random hexamers as primers. Quantitative PCR was performed with the Power SYBR PCR Master Mix (Applied Biosystems). Reactions were run on the iCycler iQ (Bio-Rad). The thermo cycling condition were: 15 min at 95° C., 40 cycles of denaturation at 95° C. for 20 s, annealing (20 s) and extension (35 s) at 72° C. Specific primer pairs, designed using the Primer3 software, are shown.

phoB:
5'-TTACGTCGTCAAGCCCTTCT-3' (SEQ ID N 1)
and
5'-CCGGTGAGGACATGAGAAAT-3' (SEQ ID N 2);

phoC:
5'-ACTCCTGCGCATGATAAACC-3' (SEQ ID N 3)
and
5'-TGTTGAGGACGCTCAGTACG-3' (SEQ ID N 4);

phoD:
5'-TATCTCGTTCCCCTCGTCAC-3' (SEQ ID N 5)
and
5'-ACCTTTGTCGACCATCTTGC-3' (SEQ ID N 6);

phoE:
5'-GCTTCATCCTGTGCTTCCTC-3' (SEQ ID N 7)
and
5'-AGACCTTCCTCCGGTTTCAT-3' (SEQ ID N 8);

phoT:
5'-TGGCGTCGTTCTTTACATGA-3' (SEQ ID N 9)
and
5'-GTCTCCTTTTCGAGCGTGAC-3' (SEQ ID N 10);

smc02641:
5'-CGAGAGGTGATGACGGAAGT-3' (SEQ ID N 11)
and
5'-ACCGACTTTCTCGCACAGAT-3' (SEQ ID N 12);

smc00128:
5'-CTTCAGCATGAACGACCAGA-3' (SEQ ID N 13)
and
5'-AAGAACCGCGTAACCTTCCT-3' (SEQ ID N 14).

smc02641 and smc00128 were used as housekeeping genes for data normalization in the comparative Ct method as previously described (8).

Phosphatase Activity

Alkaline and acid phophatase enzymes under P-limiting conditions were assayed as previously reported (16). Units are reported as nanomoles per minute per milligram of protein. Protein concentrations were determined by the Bradford's assay.

Phosphate Solubilization

The concentration of soluble phosphate was estimated using a modification of Fiske and Subarrow method as described by Saheki et al. (37).

Plant Growth Conditions

Seeds of *Medicago truncatula* cv Jemalong 2HA were surface sterilized, germinated and transferred into hydroponic units as previously reported (5). P-limiting conditions were achieved by providing a modified Jensen medium containing $CaCO_3$ 1 mM and KCl 1.1 mM instead of 7.3 mM $CaHPO_4$ and 1.1 mM $K_2HPO_4$, respectively. These plants received, only on the first week, 0.02% PR. For collection of exudates, the roots of four weeks old plants were washed, submerged in sterile water and kept in a growth chamber for 48 h. Exudates were evaporated to dryness and analysed by HPLC. The identity of peaks was confirmed by GC-MS.

Organic Acids and Phosphate Release

Based on the results obtained in the analysis of organic acids production in cultures supernatant, malic (MA), succinic (SU), fumaric (FU) and 2-hydroxyglutaric (2HG) acids were added in bacterial free medium, and soluble phosphate concentration was measured. For 1021 growth simulating conditions, 1.4 mg/l FU, 500 mg/l MA and 1 g/l SU were added. For 1021+IAA growth simulating conditions, 16 mg/l FU, 860 mg/l MA and 860 mg/l SU were added. For RD64 growth simulating conditions, 5.6 mg/l FU, 840 mg/l MA and 3.1 g/l SU were added. For Mt-1021 and Mt-RD64 growth simulating conditions, 2HG was added at final concentrations of 49.6 mg/l and 115.2 mg/l, respectively. Bacterial free medium was also treated with 0.5 mM IAA solution. A media that simulates growth is a media without bacteria or their supernatant. The media comprises only RP and the organic acids used as purified powder commercially available (SIGMA), the organic acids concentration used are that produced by the bacteria when grown in a defined media (with IAA, or without, or from RFD64).

Measurement of Organic Acids Using HPLC

The organic acids were determined by HPLC with a reverse-phase Hypersil GOLD C18 (100×4.6 mm) column (Thermo Electron Corporation). The operating conditions and quantification were previously described (20).

GC-MS Analysis

Organic acid fractions collected from HPLC were dried, derivatized to their tert-butyldimethylsilyl (tBDMS) derivatives and analysed on a Micromass GCT mass spectrometer (Waters corp, Manchester, UK) coupled to an Agilent 6890 Series gas chromatograph fitted with 7683 auto-sampler (Agilent Technologies, Palo Alto, Calif.) and ZB-5 ms (Phenomenex, Macclesfield, UK) caplillary column (30 m×0.25 mm I.D.×0.25 μm d.f. with 5 m Guardian). Samples were injected using splitless injection technique at 250° C. and a helium gas flow of 2.0 ml min$^{-1}$. The oven was set at 70° C. for 2 min, then ramped at 7° C. min$^{-1}$ to 350° C. and held for 5 min. The GC interface and source temperatures were set to 250° C. and EI$^+$ mass spectra were acquired at 70 eV from 0 to 47 min with an acquisition rate of 1 spectra/sec. Chromatographic peaks were identified either from existing mass spectral and retention time data from standards previously analysed at Rothamsted Research LTD (Harpenden Herts, UK) or from the NIST mass spectral database in conjunction with retention data obtained from the literature (30). Determination of the accurate mass, to within 5 ppm, of M$^+$, M-15$^+$, M-57$^+$ was used to verify analyte identifications. The chromatograms obtained for each sample were compared to the derivatization reagent blank.

Data Analysis

Data were subjected to statistical evaluation using one-way analysis of variance (ANOVA) and Tukey's multiple comparison Test.

Results

Regulation of pho Operon Genes.

The author have evaluated, under P-sufficient (13 mM) conditions, the global effects triggered by IAA overproduction in S. meliloti cells using a transcriptional profiling approach. The author compared the gene expression patterns of wild type 1021 with those of RD64 and 1021 treated with IAA (1021+IAA). To verify the specificity of IAA effects, the author also compared the expression patterns of 1021 untreated cells with those of four chemically or functionally similar molecules such as indole (1021+Ind), tryptophan (1021+Trp), indole-3-carboxylic acid (1021+ICA) and 2,4-dichlorophenoxyacetic acid (1021+2,4-D) (42) (Table S1 to S6).

TABLE S1

*S. meliloti 1021 genes whose relative expression level increases or decreases after treatment with 0.5 mM IAA.*

| Gene ID | Gene name | Description | M$^a$ | P Value |
|---|---|---|---|---|
| SMc01169 | ald | PROBABLE ALANINE DEHYDROGENASE OXIDOREDUCTASE PROTEIN | 3.024845281 | 0.000556412 |
| SMc02514 | smc02514 | PUTATIVE PERIPLASMIC BINDING ABC TRANSPORTER PROTEIN | 1.763677824 | 0.021591241 |
| SMb20893 | gguB | probable sugar uptake ABC transporter permease protein | 1.753795629 | 0.000556412 |
| SMb20922 | smb20922 | HYPOTHETICAL PROTEIN | 1.711383754 | 0.000222661 |
| SMc04087 | smc04087 | PUTATIVE TRANSMEMBRANE PROTEIN | 1.592749709 | 0.055113061 |
| SMb20895 | chvE | probable sugar uptake ABC transporter periplasmic solute binding protein precursor | 1.424536893 | 0.002763939 |
| SMb21183 | htpG | probable chaperonine heat shock hsp90 proteins family | 1.383579163 | 0.009776774 |
| SMa1118 | hspC2 | probable HspC2 heat shock protein | 1.295763868 | 0.054729049 |
| SMc01103 | rbsK | PROBABLE RIBOKINASE PROTEIN | 1.199865871 | 0.062047659 |
| SMc03168 | smc03168 | PUTATIVE MULTIDRUG EFFLUX SYSTEM PROTEIN | 1.164524891 | 0.032740196 |
| SMc03168 | smc03168 | PUTATIVE MULTIDRUG EFFLUX SYSTEM PROTEIN | 1.164524891 | 0.032740196 |
| SMb21197 | oppB | putative oligopeptide uptake ABC transporter permease protein | 1.111217702 | 0.03441727 |
| SMc02786 | smc02786 | PUTATIVE TRANSLOCASE TRANSMEMBRANE PROTEIN | 1.109949597 | 0.027211213 |
| SMc02729 | smc02729 | HYPOTHETICAL TRANSMEMBRANE PROTEIN | 0.894214516 | 0.077655861 |
| SMc02475 | smc02475 | PUTATIVE OUTER MEMBRANE LIPOPROTEIN PRECURSOR | 0.733925161 | 0.054292477 |
| SMc01628 | smc01628 | PUTATIVE PERIPLASMIC BINDING ABC TRANSPORTER PROTEIN | 0.712282328 | 0.060800942 |
| SMc00364 | rplT | PROBABLE 50S RIBOSOMAL PROTEIN L20 | −0.714986207 | 0.026564529 |
| SMc01309 | rplC | PROBABLE 50S RIBOSOMAL PROTEIN L3 | −0.724654269 | 0.055113061 |
| SMc00568 | rpsF | PUTATIVE 30S RIBOSOMAL PROTEIN S6 | −0.761629923 | 0.060779136 |
| SMb21177 | phoC | phosphate uptake ABC transporter ATP binding protein | −0.79391639 | 0.025150574 |
| SMc01296 | rpsN | PROBABLE 30S RIBOSOMAL PROTEIN S14 | −0.832571686 | 0.030646137 |
| SMc01295 | rpsH | PROBABLE 30S RIBOSOMAL PROTEIN S8 | −0.899568721 | 0.007947725 |
| SMc00363 | rpmI | PROBABLE 50S RIBOSOMAL PROTEIN L35 | −0.980671144 | 0.022316759 |
| SMb21174 | phoT | phosphate uptake ABC transporter permease protein | −1.206701338 | 0.008998087 |
| SMc01291 | rpmD | PROBABLE 50S RIBOSOMAL PROTEIN L30 | −1.237159143 | 0.019628185 |
| SMc01301 | rpmC | PROBABLE 50S RIBOSOMAL PROTEIN L29 | −1.272963317 | 0.007455448 |
| SMc01319 | rplJ | PROBABLE 50S RIBOSOMAL PROTEIN L10 (L8) | −1.438053855 | 0.011918941 |
| Mc01302 | rplP | PROBABLE 50S RIBOSOMAL PROTEIN L16 | −1.862233128 | 0.009776774 |

Gene ID, name and description are as reported at http://bioinfo.genopole-toulouse.prd.fr/annotation/iANT/bacteria/rhime/
$^a$The M value refers to the log$_2$ of the ratio of intensities of each spots in the two channels (21).

TABLE S2

_S. meliloti 1021 genes whose relative expression level increases or decreases after treatment with 0.5 mM Indole._

| Gene ID | Gene name | Description | $M^a$ | P Value |
|---|---|---|---|---|
| SMc04040 | ibpA | PROBABLE HEAT SHOCK PROTEIN | 2.4491133 | 4.02E−06 |
| SMc03253 | smc03253 | PUTATIVE L PROLINE 3 HYDROXYLASE PROTEIN | 1.9505191 | 2.94E−06 |
| SMc04087 | smc04087 | PUTATIVE TRANSMEMBRANE PROTEIN | 1.9437362 | 2.61E−05 |
| SMc04141 | gst9 | PUTATIVE GLUTATHIONE S TRANSFERASE PROTEIN | 1.7081209 | 7.08E−06 |
| SMa1329 | sma1329 | Putative proline dipeptidase | 1.6577909 | 4.32E−06 |
| SMc01106 | smc01106 | PROBABLE SMALL HEAT SHOCK PROTEIN | 1.51285 | 2.13E−06 |
| SMc04140 | smc04140 | PUTATIVE ATP BINDING ABC TRANSPORTER PROTEIN | 1.4108408 | 0.00363899 |
| SMb21177 | phoC | phosphate uptake ABC transporter ATP binding protein | 1.282009 | 8.09E−07 |
| SMa1128 | degP4 | DegP4 protease like protein | 1.15192 | 4.02E−06 |
| SMb21183 | htpG | probable chaperonine heat shock hsp90 proteins family | 0.9544155 | 3.16E−05 |
| SMc01312 | fusA1 | PROBABLE ELONGATION FACTOR G PROTEIN | 0.912809 | 0.00022133 |
| SMc03829 | smc03829 | PUTATIVE TRANSPORT SYSTEM PERMEASE ABC TRANSPORTER PROTEIN | 0.8604338 | 0.00071899 |
| SMc03167 | smc03167 | PUTATIVE MULTIDRUG EFFLUX SYSTEM PROTEIN | 0.7656327 | 0.00022133 |
| SMa1077 | nex18 | Nex18 Symbiotically induced conserved protein | 0.7412711 | 0.00029644 |
| SMc02857 | dnaK | HEAT SHOCK PROTEIN 70 (HSP70) CHAPERONE | 0.7321448 | 0.00024744 |
| SMa1087 | sma1087 | Putative cation transport P type ATPase | 0.7198729 | 0.00707161 |
| SMc01318 | rplL | PROBABLE 50S RIBOSOMAL PROTEIN L7/L12 (L8) | −0.703652 | 0.00024113 |
| SMc00335 | rpsA | 30S RIBOSOMAL PROTEIN S1 | −0.708311 | 0.00076724 |
| SMc01311 | tufA | PROBABLE ELONGATION FACTOR TU PROTEIN | −0.711049 | 1.03E−05 |
| SMc00383 | gst3 | PUTATIVE GLUTATHIONE S TRANSFERASE PROTEIN | −0.747804 | 0.00180021 |
| SMc03159 | smc03159 | PUTATIVE ATP BINDING ABC TRANSPORTER PROTEIN | −0.938019 | 0.00040829 |
| SMc00182 | smc00182 | PUTATIVE TRANSCRIPTION REGULATOR PROTEIN | −0.942917 | 1.96E−05 |
| SMc01946 | livK | PUTATIVE LEUCINE SPECIFIC BINDING PROTEIN PRECURSOR | −1.076561 | 7.38E−05 |
| SMc01308 | rplD | PROBABLE 50S RIBOSOMAL PROTEIN L4 | −1.252414 | 9.97E−06 |
| SMc00364 | rplT | PROBABLE 50S RIBOSOMAL PROTEIN L20 | −1.373283 | 4.18E−05 |
| SMc02501 | atpD | PROBABLE ATP SYNTHASE BETA CHAIN PROTEIN | −1.40503 | 8.30E−07 |
| SMc01291 | rpmD | PROBABLE 50S RIBOSOMAL PROTEIN L30 | −1.484709 | 1.03E−05 |
| SMc04114 | pilA1 | PUTATIVE PILIN SUBUNIT PROTEIN | −1.887557 | 2.94E−06 |

Gene ID, name and description are as reported at http://bioinfo.genopole-toulouse.prd.fr/annotation/iANT/bacteria/rhime/
$a$The M value refers to the $\log_2$ of the ratio of intensities of each spots in the two channels (21).

TABLE S3

_S. meliloti 1021 genes whose relative expression level increases or decreases after treatment with 0.5 mM Tryptophan._

| Gene ID | Gene name | Description | $M^a$ | P value |
|---|---|---|---|---|
| SMa1321 | virB1 | virB1 type IV secretion protein | 4.444843574 | 5.76E−10 |
| SMc03253 | smc03253 | PUTATIVE L PROLINE 3 HYDROXYLASE PROTEIN | 2.688816083 | 1.21E−07 |
| SMc04140 | smc04140 | PUTATIVE ATP BINDING ABC TRANSPORTER PROTEIN | 2.032282837 | 0.000658944 |
| SMb20672 | smb20672 | putative sugar uptake ABC transporter permease protein | 1.815183664 | 0.000464709 |
| SMc04141 | gst9 | PUTATIVE GLUTATHIONE S TRANSFERASE PROTEIN | 1.580678927 | 0.002877464 |
| SMa1128 | degP4 | DegP4 protease like protein | 1.449385608 | 0.002545682 |
| SMc02507 | sitC | PUTATIVE IRON TRANSPORT SYSTEM MEMBRANE ABC TRANSPORTER PROTEIN | 1.132611055 | 0.005755651 |
| SMb20585 | ggt | putative gamma glutamyltranspeptidase protein | 1.089676324 | 0.018044699 |
| SMa2189 | sma2189 | putative integrase/recombinase | 0.993022383 | 0.005634243 |
| SMa1007 | sma1007 | Copper protein putative | 0.980054843 | 0.031998986 |
| SMa2145 | sma2145 | probable aminomethyltransferase | 0.914452315 | 0.022642532 |
| SMa0707 | sma0707 | dihydrodipicolinate synthase putative | 0.908418132 | 0.046709835 |
| SMa0711 | sma0711 | putative ABC transporter permease protein MalFG family | 0.886253547 | 0.041859671 |
| SMa1118 | hspC2 | probable HspC2 heat shock protein | 0.866291958 | 0.008200888 |
| SMc04147 | smc04147 | PUTATIVE PERMEASE PROTEIN | 0.826220763 | 0.027089558 |
| SMa1087 | sma1087 | Putative cation transport P type ATPase | 0.751037358 | 0.048246323 |
| SMa1073 | sma1073 | TRm23b IS ATP binding protein | 0.742254734 | 0.025726092 |
| SMc01169 | ald | PROBABLE ALANINE DEHYDROGENASE OXIDOREDUCTASE PROTEIN | 0.737931247 | 0.023749056 |
| SMc01311 | tufA | PROBABLE ELONGATION FACTOR TU PROTEIN | −0.722897465 | 0.001153449 |
| SMc01314 | rpsL | PROBABLE 30S RIBOSOMAL PROTEIN S12 | −0.734864111 | 0.016575446 |
| SMc01313 | rpsG | PROBABLE 30S RIBOSOMAL PROTEIN S7 | −0.751779496 | 0.01095587 |
| SMc01293 | rplR 3 | PROBABLE 50S RIBOSOMAL PROTEIN L18 | −0.763652168 | 0.012690901 |
| SMc04434 | rpmH | PROBABLE 50S RIBOSOMAL PROTEIN L34 | −0.775772779 | 0.003459468 |
| SMc01636 | smc01636 | PUTATIVE TRANSCRIPTION REGULATOR PROTEIN | −0.94728054 | 0.003589821 |
| SMb21566 | groEL5 | putative heat shock protein groEL | −1.020953539 | 0.00012659 |
| SMc00182 | smc00182 | PUTATIVE TRANSCRIPTION REGULATOR PROTEIN | −1.096524292 | 0.003162499 |
| SMb20984 | nirB 4 | putative nitrite reductase [NAD(P)H] large subunit protein | −1.109685898 | 0.000376277 |
| SMc00155 | aroF | PROBABLE DAHP SYNTHETASE PROTEIN | −1.56466062 | 8.11E−05 |

Gene ID, name and description are as reported at http://bioinfo.genopole-toulouse.prd.fr/annotation/iANT/bacteria/rhime/
$a$The M value refers to the $\log_2$ of the ratio of intensities of each spots in the two channels (21).

TABLE S4

*S. meliloti* 1021 genes whose relative expression level increases or decreases after treatment with 0.5 mM ICA.

| Gene ID | Gene name | Description | $M^a$ | P Value |
|---|---|---|---|---|
| SMc01169 | ald | PROBABLE ALANINE DEHYDROGENASE OXIDOREDUCTASE PROTEIN | 1.709603089 | 0.00835282 |
| SMc02603 | smc02603 | PUTATIVE TRANSPORT TRANSMEMBRANE PROTEIN | 1.484428133 | 0.01927884 |
| SMc04040 | ibpA | PROBABLE HEAT SHOCK PROTEIN | 1.473713787 | 1.97E−05 |
| SMa1128 | degP4 | DegP4 protease like protein | 1.148294032 | 0.005172893 |
| SMc03253 | smc03253 | PUTATIVE L PROLINE 3 HYDROXYLASE PROTEIN | 1.14006745 | 0.00220191 |
| SMc04140 | smc04140 | PUTATIVE ATP BINDING ABC TRANSPORTER PROTEIN | 1.126173329 | 0.027805968 |
| SMa1118 | hspC2 | probable HspC2 heat shock protein | 1.111188207 | 0.020857534 |
| SMc04307 | cyaD2 | PUTATIVE ADENYLATE/GUANYLATE CYCLASE TRANSMEMBRANE PROTEIN | 1.011985231 | 0.00097178 |
| SMc03168 | smc03168 | PUTATIVE MULTIDRUG EFFLUX SYSTEM PROTEIN | 1.005018738 | 0.007398989 |
| SMa1077 | nex18 | Nex18 Symbiotically induced conserved protein | 0.993757572 | 0.00097178 |
| SMc00537 | smc00537 | PUTATIVE TRANSPORT PROTEIN | 0.958342276 | 0.045926511 |
| SMa1306 | virB9 | VirB9 type IV secretion protein | 0.940431647 | 0.029383575 |
| SMc01534 | smc01534 | PUTATIVE OMEGA AMINO ACID PYRUVATE AMINOTRANSFERASE PROTEIN | 0.927685887 | 0.007398989 |
| SMc03829 | smc03829 | PUTATIVE TRANSPORT SYSTEM PERMEASE ABC TRANSPORTER PROTEIN | 0.906503799 | 0.010242834 |
| SMc00514 | smc00514 | PUTATIVE MONOOXYGENASE PROTEIN | 0.872057618 | 0.028207167 |
| SMb21183 | htpG | probable chaperonine heat shock hsp90 proteins family | 0.7619012 | 0.030552462 |
| SMc03037 | flaA | FLAGELLIN A PROTEIN | −0.71144865 | 0.008867601 |
| SMc00323 | rpsO | PROBABLE 30S RIBOSOMAL PROTEIN S15 | −0.72195502 | 0.008965819 |
| SMc04114 | pilA1 | PUTATIVE PILIN SUBUNIT PROTEIN | −0.72744163 | 0.018953535 |
| SMc02498 | atpH | PUTATIVE ATP SYNTHASE DELTA CHAIN PROTEIN | −0.72807496 | 0.003920621 |
| SMc03030 | flgG | FLAGELLAR BASAL BODY ROD PROTEIN | −0.75006865 | 0.036232645 |
| SMc01309 | rplC | PROBABLE 50S RIBOSOMAL PROTEIN L3 | −0.75579918 | 0.008143182 |
| SMc01793 | smc01793 | PUTATIVE GLYCOSYLTRANSFERASE PROTEIN | −0.76252145 | 0.005300736 |
| SMc00335 | rpsA | 30S RIBOSOMAL PROTEIN S1 | −0.776312 | 0.018932734 |
| SMc00868 | atpF | PROBABLE ATP SYNTHASE B CHAIN TRANSMEMBRANE PROTEIN | −0.83061618 | 0.011065196 |
| SMc00913 | groEL1 | 60 KD CHAPERONIN A PROTEIN | −0.83494684 | 0.039308482 |
| SMc01326 | tufB | PROBABLE ELONGATION FACTOR TU PROTEIN | −0.87682266 | 0.012773579 |
| SMc00912 | groES1 | 10 KD CHAPERONIN A PROTEIN | −1.49142677 | 0.004572783 |

Gene ID, name and description are as reported at http://bioinfo.genopole-toulouse.prd.fr/annotation/iANT/bacteria/rhime/
$^a$The M value refers to the $\log_2$ of the ratio of intensities of each spots in the two channels (21).

TABLE S5

*S. meliloti* 1021 genes whose relative expression level increases or decreases after treatment with 0.5 ml\4 2,4-D.

| Gene ID | Gene name | Description | $M^a$ | P Value |
|---|---|---|---|---|
| SMa1077 | nex18 | Nex18 Symbiotically induced conserved protein | 2.58085875 | 0.03163763 |
| SMa1128 | degP4 | DegP4 protease like protein | 1.55249531 | 0.01374723 |
| SMb21221 | smb21221 | putative sugar uptake ABC transporter periplasmic solute binding protein precursor | 1.02658325 | 0.03928731 |
| SMc03805 | tesB | PROBABLE ACYL COA THIOESTERASE II PROTEIN | 0.99913786 | 0.05718535 |
| SMc00591 | smc00591 | HYPOTHETICAL/UNKNOWN SIGNAL PEPTIDE PROTEIN | 0.86290789 | 0.03042775 |
| SMc03859 | rpsP | PROBABLE 30S RIBOSOMAL PROTEIN S16 | −0.7103949 | 0.04708837 |
| SMc00335 | rpsA | 30S RIBOSOMAL PROTEIN S1 | −0.7145391 | 0.04366812 |
| SMc02905 | dnaX | PUTATIVE DNA POLYMERASE III SUBUNIT TAU PROTEIN | −0.726406 | 0.03042775 |
| SMc00363 | rpmI | PROBABLE 50S RIBOSOMAL PROTEIN L35 | −0.8021142 | 0.04684434 |
| SMc02717 | leuA1 | 2 ISOPROPYLMALATE SYNTHASE PROTEIN | −0.8087469 | 0.00997117 |
| SMc02692 | rplY | PUTATIVE 50S RIBOSOMAL PROTEIN L25 | −0.8486084 | 0.00716822 |
| SMc00151 | gph1 | PROBABLE PHOSPHOGLYCOLATE PHOSPHATASE PROTEIN | −0.8712822 | 0.00723807 |
| SMc01883 | smc01883 | HYPOTHETICAL TRANSMEMBRANE PROTEIN | −0.8788488 | 0.03163763 |
| SMc01300 | rpsQ | PROBABLE 30S RIBOSOMAL PROTEIN S17 | −0.9523795 | 0.00226024 |
| SMc01291 | rpmD | PROBABLE 50S RIBOSOMAL PROTEIN L30 | −0.9964348 | 0.03465032 |
| SMc01214 | smc01214 | PUTATIVE ZINC CONTAINING ALCOHOL DEHYDROGENASE PROTEIN | −1.0392929 | 0.03653619 |
| SMc03979 | gap | PROBABLE GLYCERALDEHYDE 3 PHOSPHATE DEHYDROGENASE PROTEIN | −1.0652513 | 0.05688975 |
| SMc01858 | smc01858 | CONSERVED HYPOTHETICAL PROTEIN | −1.0825725 | 0.01522216 |
| SMc02498 | atpH | PUTATIVE ATP SYNTHASE DELTA CHAIN PROTEIN | −1.2509153 | 0.01508863 |
| SMc01298 | rplX | PROBABLE 50S RIBOSOMAL PROTEIN L24 | −1.2601536 | 0.01930926 |
| SMc00912 | groES1 | 10 KD CHAPERONIN A PROTEIN | −1.2715839 | 0.04708837 |
| SMc00869 | atpF2 | PROBABLE ATP SYNTHASE SUBUNIT B' TRANSMEMBRANE PROTEIN | −1.3178757 | 0.00726489 |
| SMc04003 | rpmJ | PROBABLE 50S RIBOSOMAL PROTEIN L36 | −1.331155 | 0.00346374 |
| SMc02340 | smc02340 | PUTATIVE TRANSCRIPTION REGULATOR PROTEIN | −1.4082815 | 0.01027773 |
| SMc01299 | rplN | PROBABLE 50S RIBOSOMAL PROTEIN L14 | −1.5873658 | 0.00366764 |
| SMc01326 | tufB | PROBABLE ELONGATION FACTOR TU PROTEIN | −1.6636138 | 0.00282898 |

TABLE S5-continued

*S. meliloti* 1021 genes whose relative expression level increases or decreases after treatment with 0.5 ml\4 2,4-D.

| Gene ID | Gene name | Description | $M^a$ | P Value |
|---|---|---|---|---|
| SMc01319 | rplJ | PROBABLE 50S RIBOSOMAL PROTEIN L10 (L8) | −1.7881878 | 1.40E−06 |
| SMc01301 | rpmC | PROBABLE 50S RIBOSOMAL PROTEIN L29 | −2.0066958 | 0.00366764 |

Gene ID, name and description are as reported at http://bioinfo.genopole-toulouse.prd.fr/annotation/iANT/bacteria/rhime/
$^a$ The M value refers to the $\log_2$ of the ratio of intensities of each spots in the two channels (21).

TABLE S6

*S. meliloti* RD64 genes whose relative expression level increases or decreases as compared to wild-type strain.

| Gene ID | Gene name | Description | $M^a$ | P value |
|---|---|---|---|---|
| SMc04087 | smc04087 | Putative transmembrane protein | 1.99884592 | 9.19E−05 |
| SMc01095 | mexF1 | Probable multidrug efflux system transmembrane protein | 1.53758894 | 1.42E−06 |
| SMc03245 | smc03245 | Putative amidase protein | 1.25311085 | 0.000236703 |
| SMc01106 | smc01106 | Probable small heat shock protein | 1.18271524 | 0.000425479 |
| SMc03208 | hmgA | Homogentisate 12 dioxygenase protein | 1.12512665 | 2.30E−05 |
| SMc03805 | tesB | Probable acyl CoA thioesterase II protein | 0.98314209 | 3.25E−05 |
| SMb21216 | smb21216 | Putative sugar uptake ABC transporter ATP binding protein | 0.89780301 | 0.043969901 |
| SMb21183 | htpG | Probable chaperonine heat shock hsp90 proteins family | 0.89755767 | 0.002792969 |
| SMc02610 | glxB | Putative amidotransferase protein | 0.85161643 | 4.73E−06 |
| SMb21295 | smb21295 | Putative small heat shock protein hsp20 family | 0.84263999 | 3.98E−05 |
| SMb21221 | smb21221 | Putative sugar uptake ABC transporter periplasmic solute binding protein precursor | 0.81363362 | 0.002008173 |
| SMc04128 | smc04128 | Putative heavy metal transporting atpase protein | 0.78120181 | 0.001972893 |
| SMc02576 | smc02576 | Hypothetical acetyltransferase protein | 0.72720949 | 7.11E−05 |
| SMc01326 | tufB | Probable elongation factor tu protein | −0.7141322 | 0.000873039 |
| SMc00868 | atpF | Probable atp synthase b chain transmembrane protein | −0.7170929 | 2.43E−08 |
| SMc00335 | rpsA | 30S ribosomal protein S1 | −0.7502647 | 0.000335846 |
| SMc00871 | atpB | Probable ATP synthase A chain transmembrane protein | −0.8088227 | 0.000995828 |
| SMb21177 | phoC | Phosphate uptake ABC transporter ATP binding protein | −0.8306733 | 2.95E−06 |
| SMc01309 | rplC | Probable 50s ribosomal protein L3 | −0.8348891 | 1.76E−09 |
| SMc00870 | atpE | Probable ATP synthase subunit C transmembrane protein | −0.863293 | 4.11E−05 |
| SMc02498 | atpH | Putative ATP synthase delta chain protein | −1.006709 | 3.98E−05 |
| SMc01301 | rpmC | Probable 50S ribosomal protein L29 | −1.0467565 | 4.33E−07 |
| SMc01291 | rpmD | Probable 50S ribosomal protein L30 | −1.1945951 | 1.42E−06 |
| SMc01285 | rpoA | Probable DNA directed RNA polymerase alpha chain protein | −1.2449298 | 5.71E−06 |
| SMc01319 | rp1J | Probable 50S ribosomal protein L10 (L8) | −1.2628004 | 2.95E−06 |
| SMc01302 | rplP | Probable 50S ribosomal protein L16 | −1.3323341 | 2.94E−06 |
| SMc01804 | rplM | Probable 50S ribosomal protein L13 | −1.3616399 | 0.000193529 |
| SMc01830 | ureG | Probable urease accessory protein | −1.3746456 | 1.35E−05 |

Gene ID, name and description are as reported at http://bioinfo.genopole-toulouse.prd.fr/annotation/iANT/bacteria/rhime/
$^a$ The M value refers to the $\log_2$ of the ratio of intensities of each spots in the two channels (21).

For the genes of the phoCDET operon that code for the high-affinity phosphate uptake system (40) the author found that the phoC was repressed in RD64 as compared to the untreated wild type 1021 cells (Tables S1). The treatment of 1021 with IAA led to a down-regulation of both phoC and phoT genes (Table S6). In contrast, when 1021 cells were treated with Ind, an up-regulation of the phoC gene was observed as compared to the untreated 1021 cells (Table S2). Concerning the addition of Trp, ICA and 2,4-D the author did not find any pho genes among those significantly affected (Tables S3 to S5). Quantitative reverse transcription polymerase chain reaction (qRT-PCR) analysis confirmed these data for RD64, 1021+IAA and 1021+Ind cells (FIG. S1) and moreover, showed that the phoB regulatory gene (4) was down-regulated in RD64 and 1021+IAA cells whereas it was unaffected in 1021+Trp, 1021+ICA and 1021+2,4-D cells, when compared to the untreated 1021 cells.

When Tip was added to RD64 cells, the expression of pho genes was unaffected or slightly reduced as compared to untreated RD64 cells (data not shown). These results suggest that the IAA overproduction in RD64 cells do not lead to Trp starvation.

RT-PCR was, then, employed to analyze the differential expression patterns of pho operon genes under P-starved conditions. The expression level of all five pho genes was highly induced in RD64 and 1021+IAA cells, whereas it was only slightly induced or unchanged in 1021+Ind and 1021+Trp cells when compared to control (FIG. 1).

Phosphatase Enzymes Activity.

Since P limitation in *Rhizobium* can result in the induction of phosphatase enzymes that are directly involved in the mineralization of inorganic phosphorus compound in different types of soils, and in higher P transport rates (1, 28), the transcriptional study was combined with analyses of phosphatase enzyme activity. Phosphate starvation induced an increase in acid phosphatase activity in both RD64 and 1021+IAA cells as compared to 1021 cells (FIG. 2A). Similar results were obtained when alkaline phosphatase was assayed, although the effect was less prominent (FIG. 2B). On the other hand, the activity of the two phosphatase enzymes in 1021+Ind and 1021+Trp cells was unaffected, or only slightly increased compared control (FIG. 2).

Organic Acids Production and P Solubilization.

To evaluate the ability of RD64 strain to solubilize inorganic P when PR is used as the sole P source, the amount of P released into culture media, was measured. The author shows that the soluble P concentration continuously increased for six days, reaching the highest value at day 9 and remained relatively constant thereafter (FIG. 3). Interestingly, the P concentration measured in the growth media of RD64 and 1021+IAA was up to 80% higher than that found for control cells. In contrast, the concentration of soluble P was negligible in bacteria free media with or without the addition of IAA.

In order to study the relationship between phosphate solubilization and the production of organic acids, culture supernatants were filtered and analysed by high-pressure liquid chromatography (HPLC). Three of the major peaks (FIG. S2A) were identified as malic, succinic and fumaric acids, respectively. The identification of these organic acids was confirmed by gas chromatography-mass spectrometry (GC-MS). The concentration of these acids was higher in both RD64 and 1021+IAA compared to control cells, with the highest increment observed for succinic acid (Table 7).

TABLE 7

Organic acids exuded by *S. meliloti* 1021, 1021 + IAA and RD64 cells grown on minimal medium containing 5% PR as the sole phosphate source.

| Sample | Organic acid content (mg/L) | | |
|---|---|---|---|
| | Malate | Succinate | Fumarate |
| 1021 | 50 ± 5 | 105 ± 7 | 0.14 ± 0.01 |
| 1021 + IAA | 86 ± 10 | 864 ± 79 | 1.7 ± 0.1 |
| RD64 | 84 ± 8 | 311 ± 31 | 0.56 ± 0.06 |

The IAA concentration added in 1021+IAA was 0.5 mM. All strains were grown in 1% mannitol RMM media (see Materials and methods section). The values reported in the Table are the averages±standard deviation of at least five independent biological experiments (p<0.001).

The author compared the amount of soluble P released into bacteria free medium upon external addition of malic, succinic and fumaric acids. To simulate the growth of *S. meliloti* cells the organic acids were added, into bacterial-free media, at the same relative ratios found in bacterial cultures. The author found that P solubilization was more effective when the levels of added organic acids were comparable to those measured during the growth of RD64 and 1021+IAA cells (FIG. 4A). However, the P released under these conditions (purified acid addition to the liquid medium) was lower than that released from bacterial cultures.

Mt-1021 and Mt-RD64 Plants Growth.

To evaluate the ability of *S. meliloti* to support plant growth under P-limiting conditions, Mt-1021 and Mt-RD64 plants were grown under low (0.02% PR as P source) and high P conditions, and fresh- and dry-weight were evaluated after four weeks of growth. When P-sufficient (8 mM K-phosphate) conditions were used, a significant improvement of Mt-RD64 plants growth was observed as compared to the Mt-1021 plants. The author show that for these plants an enhanced biomass production of the aerial part and of the whole root apparatus was observed (FIG. 5).

In P-starved conditions (PR as P source), the author observed a reduction of shoot and root fresh weight in—Mt-1021 plants, while for Mt-RD64 plants the differences was statistically significant only for the shoot fresh weight (FIG. 5). However, if the author compare P-limiting Mt-RD64 plants with Mt-1021 plants grown under P-sufficient conditions the absolute value of their shoot and root fresh weights was not statistically different (FIGS. 5C and D).

Under P-limiting conditions Mt-RD64 plants also showed a more highly branched root system with abundant lateral roots, but without significant changes in the primary roots length compared to control (FIG. 5B).

To assess whether the carboxylates released from the roots of Mt-RD64 plants was related to the ability of these plants to be more effective in the acquisition of P from the sparingly soluble PR, the organic acids exuded from the roots was analysed by HPLC (FIG. S2B) and GC-MS.

Mt-1021 and Mt-RD64 plants released the same carboxylates but to different levels. Indeed, Mt-RD64 plants released up to 130% more (1.5±0.1 mg g$^{-1}$ root fresh wt, n=5) 2-hydroxyglutaric acid, which is a derivative of the TCA cycle intermediate 2-ketoglutaric acid, than Mt-1021 plants (0.65±0.10 mg g$^{-1}$ root fresh wt, n=5, p<0.003).

The amount of soluble P released into the sterilized medium was also measured upon exogenous addition of different amounts of 2-hydroxyglutaric acid. Interestingly, P solubilization was the highest when the added organic acid level was comparable to that released during Mt-RD64 plant growth (FIG. 4B).

Discussion

It has been previously shown that RD64 cells: a) release higher amounts of IAA, increase nitrogen fixation and triggers the accumulation of storage compounds as PHB (poly-beta-hydroxybutyrate) and starch (21); b) exhibit improved resistance against stress conditions (5); c) show enhanced long-term cell survival (13).

Moreover, Mt-RD64 plants show an improved root nodules development (21) and are able to attenuate the local IAA imbalance by increasing the transcription of cytokinin signaling genes (6), when compared to Mt-1021 plants. These results reinforce the suggestion that modulating auxin and cytokinin levels is a key step in nodule formation (31-32, 34). Mt-RD64 plants with such properties exhibit higher salt-tolerance (5) as compared to Mt-1021 plants.

The author shows in the present invention that, under P-stress conditions RD64 strain improves mineral phosphate solubilization when compared to the wild type 1021 strain. The expression level of the phoB activator gene and all genes in the phoCDET regulon were induced in RD64 as compared to 1021, thus suggesting that the P transport rate increased via the high-affinity transport system in this strain. Similar results were obtained when 1021 cells were treated with IAA. This effect seems to be specific since the treatment with structurally or functionally similar molecules did not lead to significant alterations in gene expression. Considering that in *S. meliloti* 1021 a moderate level of activated PhoB is present even under phosphate sufficiency, the author thinks that the degree of induction observed for these genes might be far more relevant in other *S. meliloti* strains lacking the pstC1021 mutation.

Moreover, RD64 cells showed higher levels of acid phosphatase enzymes, which facilitate the hydrolysis of organic P esters. Such cells released higher amount of organic acids, known to be highly effective in mobilizing P from insoluble sources (17, 23), when compared to the untreated 1021 cells. Similar results were obtained when 1021 cells were treated with IAA. The author suggests that the excretion of higher amounts of malic, succinic and fumaric acids, three intermediates of citric acid cycle (TCA), observed for RD64 cells is connected to the enhanced activity of TCA cycle enzymes measured for these cells (21).

Under P-starved conditions, a higher biomass accumulation was observed for Mt-RD64 plants as compared to Mt-1021 plants. It is believed that this effect is linked to the release of higher amount of 2-hydroxyglutaric acid exuded from the roots of Mt-RD64 plants and to the modifications of important root architecture traits, such as root branching, observed for these plants. Indeed, it has been already reported that, the ability of plants to use insoluble P compounds can be significantly enhanced by engineering plants to produce more organic acids (27) and that IAA plays an important role in root system architecture adjustment during P-deprivation in *Arabidopsis* and other plant species (25, 26, 29, 33). In the present invention the author speculate that the TCA-cycle enzymes up-regulation occurring in RD64 cells (21) leads to a higher carboxylates production, resulting in a positive effect both in P-sufficient and P-starved conditions.

Under P-sufficient conditions, the higher carboxylates synthesis might increase the P soluble levels triggering a more efficient repression of the high-affinity P transport system. Indeed, under P-sufficient conditions, microarray analysis surprisingly shows a further down-regulation of pho genes in RD64 as compared to 1021 cells. On the contrary, under-P-starved conditions, carboxylates overproduction might guarantee the availability of minimal soluble P levels necessary to stimulate the induction of pho operon genes.

The enhanced metabolic activity and the correlated production of more carboxylates in RD64 cells might also occur in bacteroids inside root nodules. Carboxylates accumulated inside nodules of Mt-RD64 plants might be exuded from the root into the rhizosphere (as the author really found for the 2-hydroxyglutaric acid, a derivative of the TCA cycle intermediate 2-ketoglutaric acid) increasing the availability of P to plants.

The present invention demonstrates that both free-living *rhizobia* and nodulated plants with such properties are able to better overcome different stressful environmental conditions, including P-starvation. It is then believed that these abilities might be transferred into *rhizobia* nodulating legume (as *vigna* or chickpea) in order to increase plant yield. Such an application would be particularly interesting in regions where high salinity is a substantial constraint to crop production, PR deposits are widespread, but soluble P is too low, and the use of chemical N fertilizers, which strongly inhibited the symbiotic relationship between *Rhizobia* and legumes, is limited due to their cost. Finally, the combination of higher IAA release, P-solubilization and improved N-fixation could make the Mt-RD64 system a good candidate for legume-cereal intercropping.

References

1. Al-Niemi, T. S., et al., 1997. Plant Physiol. 113:1233-1242.
2. Arcand, M. M., and K. D. Schneider. 2006. An. Acad. Bras. Cienc. 78:791-807.
3. Bais, H. P., et al., 2006. Annu. Rev. Plant. Biol. 57:233-266.
4. Bardin, S. D., and T. M. Finan. 1998. Genetics 148:1689-1700.
5. Bianco, C., and R. Defez. 2009. J. Exp. Bot. 60(11):3097-107.
6. Bianco, C., E. Imperlini, and R. Defez. 2009. Plant Signaling & Behavior 4:763-765.
7. ᵃBianco, C., et al., 2006. Arch. Microbiol. 185:373-382.
8. ᵇBianco, C., et al., 2006. Microbiol. 152:2421-2431.
9. Biswas, D. R., and G. Narayanasamy. 2006. Biores. Technol. 97:2243-2251.
10. Botero, L. M., et al., 2000. Appl. Environ. Microbiol. 66:15-22.
11. Camerini, S., et al., 2004. In: European Association for Grain Legume Research (eds) Legumes for the benefit of agriculture. Nutrition and the environment. AEP, Dijon, pp 127-128.
12. Camerini, S., B. et al., 2008. Arch. Microbiol. 190:67-77.
13. Defez, R. 2006. Patent application WO2006134623, Method for increasing the survival of bacterial strains of the *Rhizobium* genus.
15. De Melo, M. P., T. C. Pithon-Curi, and R. Curi. 2004. Life Sci 75:1713-1725.
16. Deng, S., M. L. Summers, and M. L. Kahn. 1998. Arch. Microbiol. 170:18-26.
17. Dey, R., et al., 2004. Microbiol Res. 159:371-394.
18. Gyaneshwar, P., et al., 2002. Plant Soil 245:83-93.
19. Hooykaas, P. J. J., et al., 1977. J. Gen. Microbiol. 98:477-484.
20. Hwangbo, H. 2003. Curr. Microbiol. 47:87-92.
21. Imperlini, E., et al., 2009. Appl. Microbiol. Biotechnol. 83:727-738.
22. Jones, D. L. 1998. Plant Soil 205:25-44.
23. Kim, Y. H., B. Bae, and Y. K. Choung. 2005. J. Biosci. Bioeng. 99:23.
24. Krol, E., and A. Becker. 2004. Mol. Gen. Genomics 272:1-17.
25. Kuderova, A., et al., 2008. Plant Cell Physiol. 49:570-582.
26. Lambers, H., et al., 2006. Ann Bot. 98:693-713.
27. Lopez-Bucio, J., et al., 2000. Nat. Biotechnol. 18:450-453.
28. Misson, J., et al., 2005. Proc. Natl. Acad. Sci. USA 102:11934-11939.
29. Nacry, P. 2005. Plant Physiol. 138:2061-2074.
30. Ohie, T., et al., 2000. J. Chromatogr. B 746:63.
31. Oldroyd, G. E. D., and J. A. Downie. 2008. Annu Rev. Plant. Biol. 59:519-546.
32. Oldroyd, G. E. D., M. J. Harrison, and U. Paszkowski. 2009. Science 32:753-754.
33. Perez-Torres C. A., et al., 2009. Plant Signaling & Behavior 4:781-783.
35. Pernisova, M., et al., 2009. Proc. Natl. Acad. Sci. USA 106:3609-3614.
36. Pii, Y., et al., 2007. BMC Plant Biol. 7:21.
37. Rodriguez, H., and R. Fraga. 1999. Biotechnol. Adv. 17:319-339.
38. Saheki, S., et al., 1985. Anal. Biochem. 148:277-281.
39. Van Straaten, P. 2006. An. Acad. Bras. Cienc. 78:731-747.
40. Vassilev, N., M. Vassileva, and I. Nikolaeva. 2006. Appl. Microbiol. Biotechnol. 71:137-144.
41. Voegele, R. T., S. Bardin, and T. M. Finan. 1997. J. Bacteriol. 179:7226-7232.
42. Wandruszka, V. R. 2006. Geochem. Trans. 7:6.
43. Woodward, A. W., and B. Bartel. 2005. Ann. Bot. 95:707-735.
44. Yuan, Z.-C., R. Zaheer, and T. M. Finan. 2006. J. Bacteriol. 188:1089-1102.

The invention claimed is:

1. A method to provide solubilized phosphorus to a plant able to nodulate and/or to a soil surrounding a growth of said plant comprising:
   introducing a bacterium and a phosphate rock into said soil containing said plant; and
   inducing the nodulation of said plant with said bacterium,
   wherein said bacterium is *Sinorhizobium meliloti* RD64 strain (*S. meliloti* transformed with *iaaM* gene from *Pseudomonas syringae* pv. *savastanoi* and the *tms*2 gene from *Agrobacterium tumefaciens*), and
   wherein said RD64 strain has a high indole-3-acetic acid (IAA) content.

2. The method according to claim 1 wherein said bacterium is able to produce the indole-3-acetic acid (IAA) phytohormone.

3. The method according to claim 1 wherein said bacterium is contained within leguminous plant nodules.

* * * * *